(12) United States Patent
Hester

(10) Patent No.: US 6,593,910 B1
(45) Date of Patent: Jul. 15, 2003

(54) HEAD CONTROL

(76) Inventor: Robert George Hester, 28 Herbert Avenue, Wellington, Shropshire, TF1 2BP (GB)

(*) Notice: Subject to any disclaimer, the term of this patent is extended or adjusted under 35 U.S.C. 154(b) by 0 days.

(21) Appl. No.: 09/570,716

(22) Filed: May 15, 2000

(30) Foreign Application Priority Data

May 15, 1999 (GB) .............................................. 9911270

(51) Int. Cl.[7] .............................................. B60K 26/00
(52) U.S. Cl. ........................................ 345/161; 180/316
(58) Field of Search .............................. 345/156, 157, 345/158, 159, 161; 307/116; 180/65.1, 77; 248/694

(56) References Cited

U.S. PATENT DOCUMENTS

| | | | |
|---|---|---|---|
| 3,965,402 A | | 6/1976 | Mogle .......................... 318/55 |
| 4,078,627 A | | 3/1978 | Brown et al. ................. 180/6.5 |
| 4,093,037 A | * | 6/1978 | Miller, III ................... 180/316 |
| 4,281,734 A | | 8/1981 | Johnston ...................... 180/167 |
| 4,679,644 A | | 7/1987 | Loveless ...................... 180/6.5 |
| 4,767,940 A | * | 8/1988 | Tuttle .......................... 180/167 |
| 5,648,708 A | * | 7/1997 | Littlejohn .................... 180/907 |
| 5,701,968 A | * | 12/1997 | Wright-Ott et al. ........ 180/65.1 |
| 6,184,847 B1 | * | 2/2001 | Fateh et al. .................. 345/729 |
| 6,234,446 B1 | * | 5/2001 | Patterson ..................... 224/201 |
| 6,279,934 B1 | * | 8/2001 | Womack ................... 280/250.1 |

FOREIGN PATENT DOCUMENTS

| | | | |
|---|---|---|---|
| GB | 2195092 | 3/1988 | |
| JP | 2001105987 A | * 4/2001 | ........... B60R/11/02 |

OTHER PUBLICATIONS

European Search Report, Aug. 30, 2000.

* cited by examiner

Primary Examiner—Vijay Shankar
Assistant Examiner—Nitin Patel
(74) Attorney, Agent, or Firm—Ira S. Dorman

(57) ABSTRACT

A head control comprises a control plate (13) operable by a user with his head and biasing means (9, 11) for biasing the control plate to a predetermined orientation. A joystick control (19) is operably connected to the control plate (13) such that movement of the control plate by the user is communicated to the joystick control (19).

13 Claims, 2 Drawing Sheets

HEAD CONTROL

FIELD OF THE INVENTION

This invention relates to a head control such as can be used by disabled persons to control a wheelchair, computer, environmental control or other appliance.

OBJECT OF THE INVENTION

It is an object of the present invention to provide a head control, such as can be used by disabled persons, which is convenient and reliable in operation.

SUMMARY OF THE INVENTION

According to the present invention there is provided a head control comprising a control plate operable by a user with his head, biasing means for biasing the control plate to a predetermined orientation, and a joystick control operably connected to the control plate such that movement of the control plate by the user is communicated to the joystick control.

The head control may incorporate a cover incorporating a layer of foam material for cushioning the head of the user. The foam material may comprise a substantially continuous layer. The foam material may be provided with a fabric or like external covering.

The control plate may be mounted in a manner such that it is pivotable by the user. The control plate is preferably pivotably mounted with a ball-and-socket type device. The pivotal mounting therefore ideally allows pivoting in all directions.

The control plate may incorporate a connecting member for communicating movement to the joystick control. The connecting member may be fixed to the control plate, for example substantially at right angles thereto. Alternatively, the connecting member may be hinged relative to the control plate. The connecting member may communicate movement of the control plate to the joystick control in a manner which permits a certain amount of relative motion between the connecting member and the joystick control.

The control plate may be mounted intermediate a pair of side plates.

The biasing means may comprise one or more resilient bands extending between the control plate and each of the side plates.

Switch means may be provided laterally of the control plate, for example two switch means may be provided to each side of the control plate, such as in each of the side plates. The switch means may be mounted in a recess in a plate member, the recess being covered by a resilient membrane in such a manner that the switch is normally spaced from the membrane.

For a better understanding of the present invention and to show more clearly how it may be carried into effect reference will now be made, by way of example, to the accompanying drawings in which:

DESCRIPTION OF PREFERRED EMBODIMENT

Figure 1:
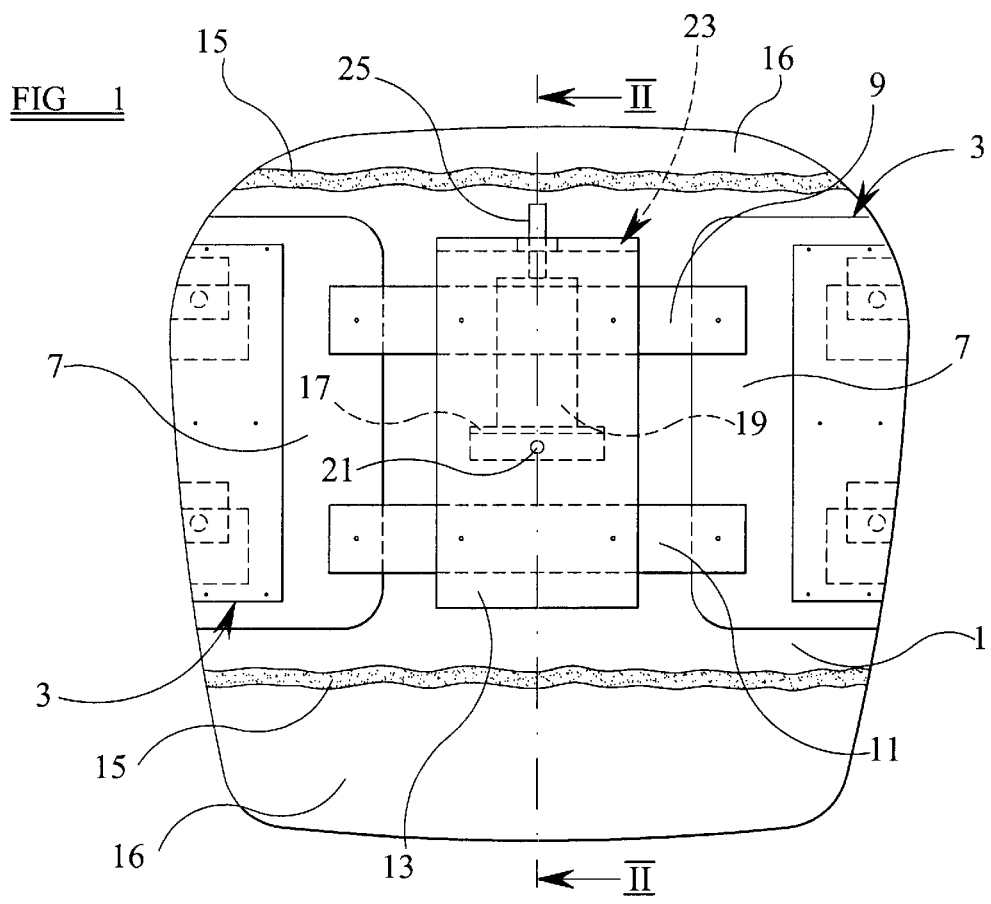
FIG. 1 is a front elevational view, partly cut away, of one embodiment of a head control according to the present invention.
Figure 2:
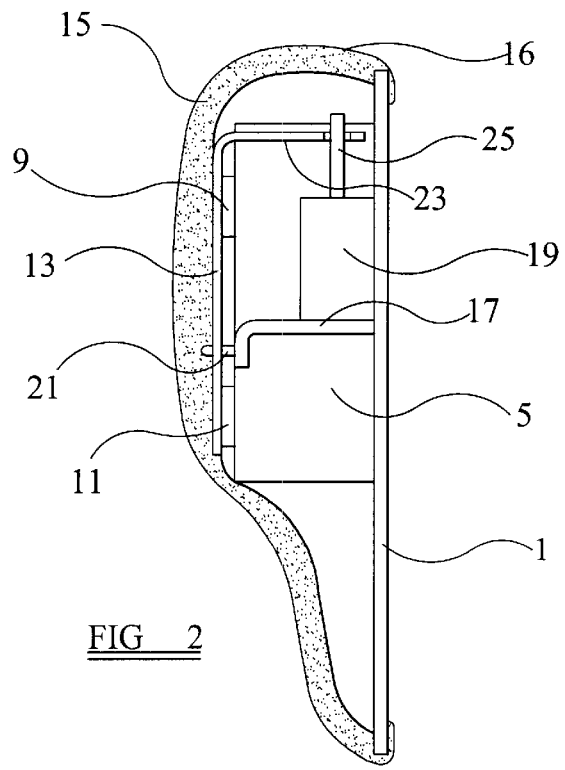
FIG. 2 is a cross-sectional view taken along the line II—II in FIG. 1.

The head control shown in FIGS. 1 and 2 comprises a back plate 1 at each side of which is mounted a contoured side plate 3. The back plate 1 facilitates mounting of the head control on a wheelchair (not shown) or the like. Each side plate comprises a forwardly extending portion 5 and a laterally inwardly extending portion 7. The portion 7 may be inclined towards the back plate 1 to provide lateral support for a user's head. Upper and lower resilient bands 9 and 11 are secured at each end thereof to the lateral portion 7 of each side plate 3 so as to be in tension. The upper and lower resilient bands are spaced apart and a generally rectangular control plate 13 is secured to the resilient bands 9 and 11 in the upper and lower regions of the control plate 13. Thus, the control plate is mounted intermediate the pair of side plates and the lateral portions 7 of the side plates 3 and the control plate 13 combine to form a slightly inwardly curved head rest for a user. For comfort, the side plates 3 and control plate 13 are covered with a continuous layer 15 of foam material and a fabric 16 or the like exterior covering.

Secured to the back plate 1 behind the control plate 13 is a supporting plate 17 on which is mounted a joystick control 19. The supporting plate 17 extends towards, but terminates short of, the control plate 13. An outer edge of the supporting plate 17 is provided with a pivotal connection 21, such as a ball-and-socket type connection, which is secured to the control plate 13. Thus, the control plate 13 is able to pivot about the pivotal connection 21, but the upper and lower resilient bands 9 and 11 bias the control plate towards a predetermined neutral position. The control plate 13 is pivotable in all directions relative to the supporting plate thus allowing pivoting about a generally horizontal axis, about a generally vertical axis and about any axis therebetween.

A connecting member 23 is provided extending between the upper edge of the control plate 13 and an operating stick 25 of the joystick control 19. The connecting member 23 extends between the control plate and the operating stick in a manner which permits a certain amount of relative motion. For example, the connecting member may be provided with an aperture through which the operating stick extends. Additionally, as an alternative to the connecting member being fixed substantially at right angles to the control plate 13, the connecting member 23 may be mounted on the control plate 13 by way of a hinged connection.

Figure 3:
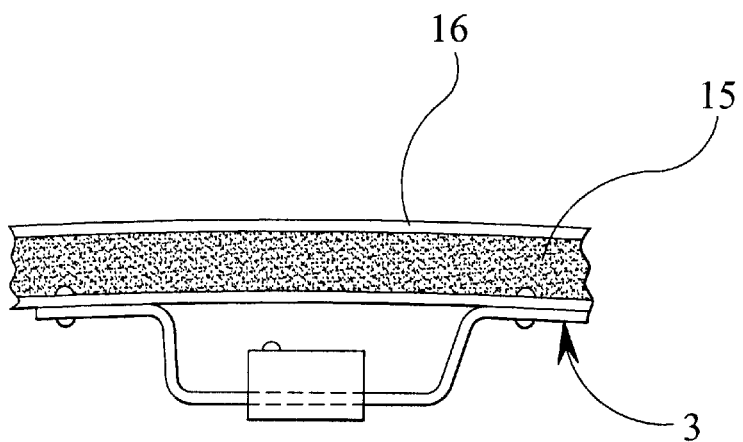
FIG. 3 is a cross-sectional view of part of a side plate of the head control shown in FIGS. 1 and 2.

As shown in FIG. 3, laterally spaced to the left and right of the control plate 13 and positioned in recesses 25 provided in each of the side plates 3 in the upper and lower regions thereof are four microswitches 27. A resilient membrane in the form of a resilient sheet 29 covers each recess and is maintained in tension thereacross with the switch spaced from the resilient sheet. The resilient sheet 29 therefore serves to prevent the layer of foam material 15 entering a recess 25 and unintentionally operating one of the microswitches 27.

Figure 4:
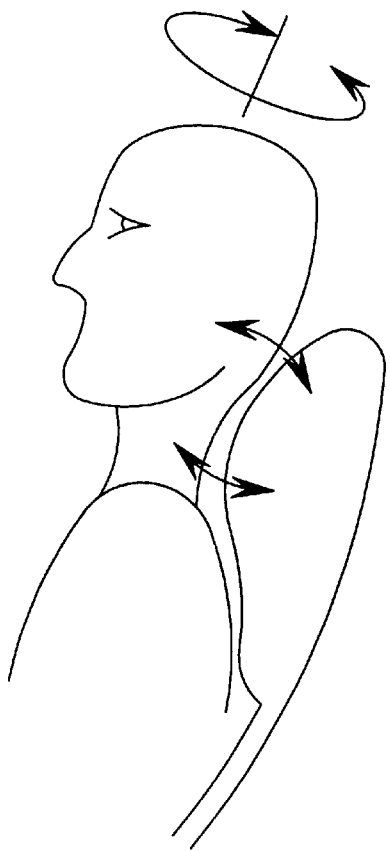
FIG. 4 is a diagrammatic illustration of the manner in which the head control according to the present invention is operated.

The head control is operated in the manner illustrated diagrammatically in FIG. 4. The control plate 13 is pivoted such that the lower region thereof is moved towards the back plate 1 by the user exerting pressure against the head control with the nape of his neck. The effect of such pressure is to move the lower region of the control plate towards the back plate and consequently to move the upper region of the control plate away from the back plate. Movement of the upper region of the control plate 13 away from the back plate 1 additionally moves the operating stick of the joystick away from the back plate.

The control plate 13 is pivoted such that the upper region thereof is moved towards the back plate 1 by the user exerting pressure against the head control with the back of his head. The effect of such pressure is to move the upper region of the control plate 13 towards the back plate 1 and thus to move the operating stick of the joystick towards the backplate.

The control plate 13 is pivoted such that the left hand region (as shown in FIG. 1) thereof is moved towards the back plate 1 by the user exerting pressure against the left hand side of the control plate by turning his head to the right. The effect of such pressure is to move the left hand side of the control plate 13 towards the back plate, to pivot the connecting member to the right (as shown in FIG. 1) and to move the operating stick of the joystick towards the right as shown in FIG. 1.

The control plate 13 is pivoted such that the right hand region (as shown in FIG. 1) thereof is moved towards the back plate 1 by the user exerting pressure against the right hand side of the control plate by turning his head to the left. The effect of such pressure is to move the right hand side of the control plate 13 towards the back plate, to pivot the connecting member 23 to the left (as shown in FIG. 1) and to move the operating stick of the joystick towards the left as shown in FIG. 1.

The control plate 13 may be pivoted in a manner which combines one of the backwards and forwards movements of the operating stick and one of the left and right movements of the operating stick by exerting pressure in one of the four corners of the control plate. Thus pressure in the upper left hand corner of the control plate 13 moves the operating stick back and to the right as shown in FIG. 1, pressure in the upper right hand corner of the control plate moves the operating stick back and to the left as shown in FIG. 1, pressure in the lower right hand corner of the control plate moves the operating stick forward and to the left as shown in FIG. 1 and pressure in the lower left hand corner of the control plate moves the operating stick forward and to the right as shown in FIG. 1.

When the user releases pressure from the control plate 11 the upper and lower resilient bands 9 and 11 pivot the control plate, and therefore the operating stick of the joystick, back to a neutral position.

The microswitches 27 are operated in a similar manner to the corners of the control plate 13 except that the user needs to stretch his head somewhat further to the side in order to operate one of the microswitches.

When attached to a wheelchair, the joystick control 19 allows, for example, control of movement of the wheelchair forwards, backwards, to the left or to the right. When the user releases pressure from the headrest the operating stick of the joystick returns to the neutral position and the wheelchair comes to a halt. The microswitches 27 can be used to control different modes of operation such as slow or fast, or can switch control to the attitude of the wheelchair seat to move the seat to any desired position between a lying position and a standing position, or can be used to control other apparatus such as a computer or environmental controls.

I claim:

1. A head control comprising a support for mounting the head control, a control plate having a plane and being pivotable about a point substantially coincident with the plane of the control plate such that the control plate is operable by a user with his head, a biasing member for biasing the control plate to a predetermined orientation relative to the support, a joystick control mounted relative to the support, and a connecting member offset relative to the pivot point of the control plate and operably connected between the control plate and the joystick control such that movement of the control plate relative to the support by the user is communicated to the joystick control.

2. A head control as claimed in claim 1 and including a cover incorporating a layer of foam material for cushioning the head of the user.

3. A head control as claimed in claim 2, wherein the foam material comprises a substantially continuous layer.

4. A head control as claimed in claim 2, wherein the foam material is provided with a fabric or like external covering.

5. A head control as claimed in claim 1, wherein the control plate is pivotable by way of a ball-and-socket type device.

6. A head control as claimed in claim 1, wherein the connecting member is fixed to the control plate.

7. A head control as claimed in claim 6, wherein the connecting member is fixed substantially at right angles to the control plate.

8. A head control as claimed in claim 1, wherein the connecting member is hinged relative to the control plate.

9. A head control as claimed in claim 1, wherein the connecting member communicates movement of the control plate to the joystick control in a manner which permits a certain amount of relative motion between the connecting member and the joystick control.

10. A head control as claimed in claim 1, wherein the control plate is mounted intermediate a pair of side plates, the biasing means extending between the control plate and each of the side plates.

11. A head control as claimed in claim 10, wherein the biasing means comprises at least one resilient band.

12. A head control as claimed in claim 1, wherein switch means is provided laterally of the control plate.

13. A head control as claimed in claim 12, wherein the switch means is mounted in a recess in a plate member, the recess being covered by a resilient membrane in such a manner that the switch is normally spaced from the membrane.

* * * * *